United States Patent

Schwab et al.

[11] Patent Number: 5,876,376
[45] Date of Patent: Mar. 2, 1999

[54] CATHETER BALLOON BONDING STOPPER

[75] Inventors: Sharon Schwab; Leslie Le; Maria D. Amores; Maritess E. Minas, all of San Diego, Calif.

[73] Assignee: Medtronic, Inc, Minneapolis, Minn.

[21] Appl. No.: 762,637

[22] Filed: Dec. 9, 1996

[51] Int. Cl.⁶ ................................................. A61M 29/00
[52] U.S. Cl. ........................... 604/103; 604/96; 604/104; 606/192
[58] Field of Search ..................... 604/96, 103; 606/192, 606/194

[56] References Cited

U.S. PATENT DOCUMENTS

| | | | |
|---|---|---|---|
| 3,884,242 | 5/1975 | Bazell et al. | 604/103 |
| 4,003,382 | 1/1977 | Dyke | 604/103 |
| 4,168,710 | 9/1979 | Rosenberg | 604/103 |
| 4,301,803 | 11/1981 | Handa et al. | 604/103 |
| 4,406,653 | 9/1983 | Nunez | 604/103 |
| 4,944,745 | 7/1990 | Sogard et al. | 604/103 |
| 5,100,381 | 3/1992 | Burns | 604/103 |
| 5,195,972 | 3/1993 | Inoue | 604/103 |
| 5,267,959 | 12/1993 | Forman | 604/103 |
| 5,397,305 | 3/1995 | Kawula et al. | 604/103 |
| 5,454,788 | 10/1995 | Walker et al. | 604/103 |
| 5,549,557 | 8/1996 | Steinke et al. | 604/103 |
| 5,569,201 | 10/1996 | Burns. | |

FOREIGN PATENT DOCUMENTS

| | | |
|---|---|---|
| 0512359 | 11/1992 | European Pat. Off. . |
| 0540858 | 5/1993 | European Pat. Off. . |

*Primary Examiner*—Wynn Wood Coggins
*Assistant Examiner*—Jennifer R. Sadula
*Attorney, Agent, or Firm*—Dianne Plunkett Latham; Harold R. Patton

[57] ABSTRACT

A medical catheter comprising a catheter shaft defining an inflation lumen and a guidewire shaft defining a guidewire lumen. The guidewire shaft is coaxial with the catheter shaft and runs longitudinally through the catheter shaft extending distally beyond the distal end of the catheter shaft. The catheter has an inflatable balloon having a proximal tail and a distal tail. The proximal tail is mounted at the distal end of the catheter shaft, the distal tail is mounted on the guidewire shaft. The balloon is in fluid communication with the inflation lumen. A distal stopper is sealingly affixed between the outer diameter of the guidewire shaft and the inner diameter of the distal tail. A proximal stopper is sealingly affixed between the outer diameter of the catheter shaft and the inner diameter of the proximal tail. The distal and proximal stopper are annular in shape and are in length shorter than the balloon tail and are of uniform circumferential thickness. An adhesive seals a portion of the tails to the catheter shaft.

24 Claims, 1 Drawing Sheet

CATHETER BALLOON BONDING STOPPER

FIELD OF THE INVENTION

The present invention relates to angioplasty catheters, and more particularly, to a catheter balloon bond at the balloon proximal or distal end.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The original catheter can then be withdrawn and a catheter of a different size or another device such as an atherectomy device can be inserted.

Conventional angioplasty balloons fall into high, medium, and low pressure ranges. Low pressure balloons are those that have burst pressures below 6 atmospheres ($6.1 \times 10^5$ Pascals). Medium pressure balloons are those that have burst pressures between 6 and 12 atm ($6.1 \times 10^5$ and $1.2 \times 10^6$ Pa). High pressure balloons are those that have burst pressures above 12 atm ($1.2 \times 10^6$ Pa). Burst pressure is determined by such factors as wall thickness and tensile strength, for example.

High pressure balloons are desirable because they have the ability to exert more force and crack hard lesions. High pressure balloons are also useful in stent deployment. A biocompatible metal stent props open blocked coronary arteries, keeping them from reclosing after balloon angioplasty. A balloon of appropriate size and pressure is first used to open the lesion. The process is repeated with a stent crimped on a high pressure balloon. The stent is deployed when the balloon is inflated. A high pressure balloon is useful for stent deployment because the stent must be forced against the artery's interior wall so that it will fully expand thereby precluding the ends of the stent from hanging down into the channel encouraging the formation of thrombus.

Many bonding techniques for bonding a balloon to a shaft, as for example, laser welding or heat bonding, require thermally similar materials. Adhesive bonds are useful when bonding materials that have different thermal characteristics. For example, a polyethylene terephthalate (PET) high pressure balloon cannot be heat or laser bonded to a polyethylene (PE) shaft because their melt points are not compatible. For performance reasons a shaft and balloon made of thermally dissimilar materials which cannot be heat or laser bonded to the balloon may be desirable. The advantage of adhesive bonds is a common bonding method for thermally dissimilar materials.

U.S. Pat. No. 4,406,653 to Nunez discloses a method and apparatus for a catheter-balloon assembly wherein the catheter balloon is mounted on the catheter by means of adhesive and, in the preferred mode, an annular internal rib protrusion of the catheter balloon is provided for forming a sharply defined boundary of adhesive thereby aiding in the even and symmetrical inflation of the catheter balloon.

Concentric bonding of coaxial shafts often result in eccentric, inconsistent bonds which can result in bond failure. Some devices use a manufacturing fixture to align the coaxial shafts. External fixtures typically hold the outer diameters of the two shafts and insert one into the other. Shaft diameter, wall thickness and concentricity variation can still result in inconsistent bonds.

Adhesives may wick past the end of the shaft into an unintended lumen. To remedy this some adhesive bonds are lengthened to minimize the chance of the adhesive wicking past the end of the lumen. The presence of an elongated stiff section of adhesive can be a disadvantage with respect to catheter flexibility and trackability. The shorter the bond the easier it is to negotiate a torturous path. What is needed is a balloon bond which minimizes bond length and thereby optimizes flexibility as well as withstands internal pressure of at least 500 psi without leaking or rupturing and which is relatively easy, consistent and reliable to manufacture.

SUMMARY OF THE INVENTION

The above features and advantages of the present invention, as well as others, are accomplished by providing a medical catheter comprising a catheter shaft defining an inflation lumen and a guidewire shaft defining a guidewire lumen. The guidewire shaft is coaxial with the catheter shaft and runs longitudinally through the catheter shaft extending distally beyond the distal end of the catheter shaft. The catheter has an inflatable balloon having a proximal tail and a distal tail. The proximal tail is mounted at the distal end of the catheter shaft, the distal tail is mounted on the guidewire shaft. The balloon is in fluid communication with the inflation lumen. A distal stopper means is sealingly affixed between the outer diameter of the guidewire shaft and the inner diameter of the distal tail. A proximal stopper means is sealingly affixed between the outer diameter of the catheter shaft and the inner diameter of the proximal tail. The distal and proximal stopper means are annular in shape and are in length shorter than the balloon tail and are of uniform circumferential thickness. An adhesive seals a portion of the tails to the catheter shaft.

DETAILED DESCRIPTION OF THE PREFERRED EMBODIMENTS

Figure 1:
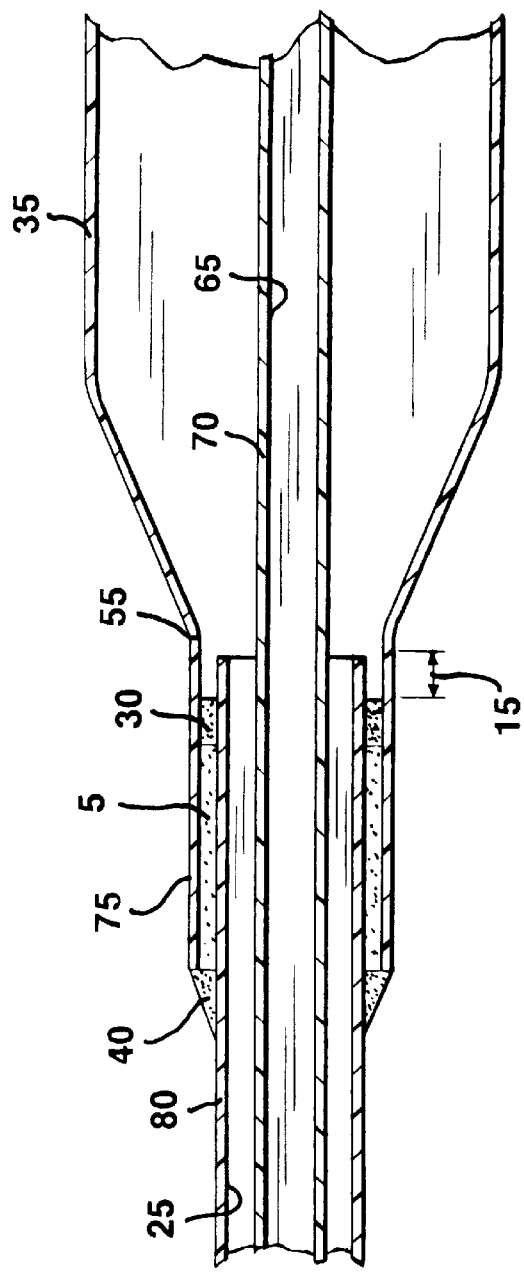
FIG. 1 is a longitudinal cross section of the proximal end of the balloon of the present invention.
Figure 2:
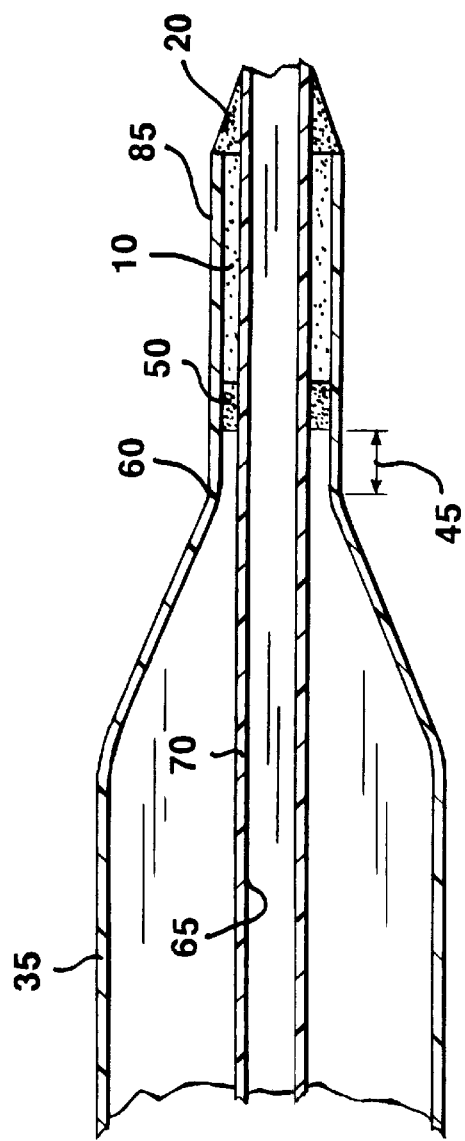
FIG. 2 is a longitudinal cross-section of the distal end of the balloon.

The present invention provides a catheter balloon proximal or distal bond stopper which minimizes bond length while reliably withstanding internal pressures of at least 500 psi pressure without leaking or rupturing and which is relatively easy, consistent and reliable to manufacture. FIGS. 1–2 are longitudinal cross-sectional views of a high pressure balloon catheter adapted for use in percutaneous transluminal coronary angioplasty (PTCA). FIG. 1 represents the proximal bond stopper 30. FIG. 2 represents the distal bond stopper 50.

The proximal and distal bonds set forth herein were designed to solve problems resulting from the bonding of coaxial shafts. The bonds center the two shafts which results in a uniform concentric alignment. The "positive stop" provided by a stopper is important to obtain a uniform gap into which adhesive can be dispensed. The invention also serves to stop the flow of adhesive past a defined point which is critical in balloon bonding since the presence of adhesive in the balloon/shaft area can adversely affect balloon in/deflation and balloon burst strength. A setback between the stopper and the end of the balloon cone increases the burst strength of the balloon and is necessary for high pressure balloons.

Since most catheter concentric proximal bonds of coaxial shafts have bond gaps of less than 0.005 inches between the distal end of the catheter shaft and the proximal end of the balloon tail, thin, low viscosity adhesives are typically used. The thinner the adhesive, the more important the use of the bonding stopper. With applicant's proximal bonding stopper 30 and distal bonding stopper 50, the bond length is controllable and therefore repeatable and more reliable. Without a uniform bond, the adhesive may flow past the desired bond length and may result in a blocked shaft and in/deflation problems.

The balloon 35 seen in FIG. 1 comprises shaft tubing 80 made of 50% HDPE/50% LDPE, a coaxial inner guidewire shaft 70 made of HDPE defining a guidewire lumen 65 and a balloon 35 made of any material suitable for high pressures above 12 atm such as PET, PET blends or Nylon. The balloon 35 necks are trimmed to between approximately 1.5 mm to 4.0 mm at the proximal and distal ends. Bonding surfaces may be plasma treated to facilitate bonding.

To prevent adhesive leakage into the balloon 35 a proximal bond stopper 30 and/or a distal bond stopper 50 may be used. The stoppers 30, 50 form a slight interference fit with the balloon 35 and can be made from any conventional adhesive suitable for balloon bonding, or from any conventional radiopaque materials or from any heat shrinkable materials. The bond stoppers 30 or 50 can also be made by using a preform.

The dimensions of the stoppers 30, 50 whether they be radiopaque, heat shrinkable, adhesive or preform, will depend on the size of the catheter shaft 80 outer diameter, the guidewire shaft 70 outer diameter and the proximal balloon cone proximal end 55 and the distal balloon cone distal end 60 inner diameters. The difference between the proximal balloon cone proximal end 55 inner diameter and the catheter shaft 80 outer diameter gives the approximate thickness of the proximal bond stopper 30. The difference between the distal balloon cone distal end 60 inner diameter and the guidewire shaft 70 outer diameter gives the approximate thickness of the distal stopper 50. A typical stopper 30, 50 will range in thickness between 0.003 inches and 0.009 inches. Typically the LDPE shaft 80 which defines the inflation lumen 25 has a outer diameter of 0.0355 inches and an inner diameter of 0.028 inches. The guidewire shaft 70 typically has an outer diameter of 0.023 inches and an inner diameter of 0.017 inches to accommodate 0.014 inch guidewires.

Create stoppers 30, 50 for catheters using conventional 0.014 inch guidewires as follows. Load a 0.030 inch mandrel into the distal end of shaft 80 for support during stopper bonding. Locate the proximal bond stopper 30 over the distal end of the shaft 80 anywhere from flush with the distal end of shaft 80 to a proximal bond setback 15 of approximately 0.25 mm to 0.5 mm. The setback 15 increases the burst strength of the balloon and is preferable for high pressure balloons. Insert the distal end of the guidewire shaft 70 into the shaft tubing 80 such that the distal end of the guidewire shaft 70 extends beyond the distal end of the shaft tubing 80. The distal end of the shaft 80 should align with the proximal end of the proximal balloon cone 55. Locate the distal bond stopper 50 over the distal end of the guidewire shaft 70 anywhere from flush with the distal end of shaft 70 to a distal bond setback 45 of approximately 0.25 mm to 0.5 mm. The distal bond setback 45 increases the burst strength of the balloon and is preferable for high pressure balloons. A variety of catheter tip configurations may be used with the distal bond stopper 50.

The setback 15 or 45 is advantageous because it is reduces the difference in thickness, hardness or stiffness between the relatively stiff high pressure balloon 35 material and the relatively soft PE shaft 80. Abrupt changes in transition result in areas where kinking is likely. Additionally, bond strength is improved because the setback 15, 45 provides a longer "lever" or effective cone angle. The longer the setback 15, 45, and the longer the balloon cone angle, the less will be the peel force of the balloon neck separating from the shaft when under high pressure. Using a proximal bond setback 15 is more important than using a distal bond setback 45 as the proximal bond typically bursts before the distal bond does. This is because typically the proximal balloon neck wall thickness is thinner than the distal neck wall thickness and therefore is not as strong. The difference in wall thickness results from the proximal balloon neck inner diameter being typically larger than the distal neck inner diameter. Typically the proximal balloon neck is sized to fit the catheter guidewire shaft and inflation shaft whereas the distal balloon neck is sized to fit only the guidewire shaft. When the balloon is formed this difference in diameter results in wall thickness difference. The distal bond setback 45 is also less critical than the proximal bond setback 15 since for geometry reasons it is advantageous to eliminate anything that is unnecessary in the distal tip region so as to reduce tip length and profile.

If a heat shrinkable material is used for stoppers 30, 50 such as PE, heat shrink the stoppers 30, 50 using any conventional means. Adhesive stoppers may be less preferred than heat shrinkable stoppers if the adhesive viscosity is such that it creates the potential for adhesive migration before the adhesive dries. To reduce the likelihood of adhesive migration, adhesives with a viscosity which approaches a gel are preferred.

If radiopaque materials such as platinum, iridium, gold, gold plated metal or combinations thereof, are used for stoppers 30, 50 they can be adhesively bonded to the catheter shaft 80 and to the guidewire shaft 70 respectively by using conventional cyannoacrylates as described below. The advantage of radiopaque stoppers is that the physician can flouroscopically view the progress of the balloon.

To create adhesive stoppers use a fast curing adhesive such as cyanoacrylate e.g., Loctite® 4061, a medical grade adhesive manufactured by Loctite Corp. in Hartford Conn. The preferred adhesive would require only one application and would be cured instantly. Loctite® 447 (600 cP) is suitable for forming the stopper in one application. Other possible Loctite® adhesives include 454 (gel), 4981 (700 cP), 4161 (1500 cP), 3091 (6000 cP), 3321 (5000 cP), 3211 (1000 cP). Dymax® Corporation of 51 Greenwoods Rd., Torrington, Conn. has ultraviolet (UV) adhesives which may also be suitable.

The adhesive stoppers 30, 50 could be created using a conventional means such as a rotating fixture. Adhesive will be dispensed onto the catheter shaft 80 or onto the guidewire shaft 70 which is rotated through 360 degrees to create a complete uniform ring of adhesive approximately 0.5 mm wide. Create an adhesive stopper 30, 50 on the shaft tubing 80 or guidewire shaft 70 respectively which is approximately 0.002 mm high around the circumference. It is important for the shaft 70, 80 to continue rotating several seconds after dispensing the adhesive to ensure uniform application until the adhesive reaches "fixture-cure" or "complete-cure" and is dry. If UV adhesive is used, activate the ultraviolet light source.

To create a preform stopper 30, 50 one could use a radiopaque marker band which is preformed to a desired dimension or a polymer or elastomer o-ring or band that is premolded or extruded to the desired dimension.

Regardless of the stopper material used (heat shrinkable, radiopaque, adhesive or preform), the following applies. The stoppers 30, 50 should be trimmed to a length of approximately 0.5 mm plus or minus 0.25 mm. The distal 1.5 mm of the balloon proximal tail is placed over the distal end of the distal shaft tubing 80. Fill the proximal bond 5 area proximal to the proximal bond stopper 30 with enough adhesive to fill the 0.002–0.003 inch gap between the proximal end of the proximal stopper 30 and the proximal end of the balloon proximal tail 75. UR-0531 or UR-2187 can be used and is available from H. B. Fuller of St. Paul, Minn. The distal 1.5 mm of the balloon distal tail 85 is placed over the distal end of the guidewire shaft tubing 70. Fill the distal bond 10 area proximal to the distal bond stopper 50 with enough adhesive to fill the 0.002–0.003 inch gap between the proximal end of the distal stopper 50 and the proximal end of the balloon distal tail 85. UR-0531 or UR-2187 can be used available from H. B. Fuller of St. Paul, Minn. Add more adhesive (such as UR-0531 or UR-2187 available from H. B. Fuller) to form a proximal bond adhesive fillet 40 and a distal bond fillet 20 which is from about 0.75 mm long to about 1 mm long. The fillets 20 and 40 taper down to the distal end of the guidewire shaft 70 and down to the shaft tubing 80 respectively.

The preceding specific embodiments are illustrative of the practice of the invention. It is to be understood, however, that other expedients known to those skilled in the art or disclosed herein, may be employed without departing from the appended claims.

| No. | Component |
| --- | --- |
| 5 | Proximal Bond Adhesive |
| 10 | Distal Bond Adhesive |
| 15 | Proximal Bond Setback |
| 20 | Distal Bond Adhesive Fillet |
| 25 | Inflation Lumen |
| 30 | Proximal Bond Stopper |
| 35 | Balloon |
| 40 | Proximal Bond Adhesive Fillet |
| 45 | Distal Bond Setback |
| 50 | Distal Bond Stopper |
| 55 | Proximal Balloon Cone Proximal End |
| 60 | Distal Balloon Cone Distal End |
| 65 | Guidewire Lumen |
| 70 | Guidewire Shaft |
| 75 | Proximal Tail |
| 80 | Catheter Shaft |
| 85 | Distal Tail |

What is claimed is:

1. A medical catheter comprising:
   a catheter shaft defining an inflation lumen, the catheter shaft having an inner diameter, outer diameter, proximal end and distal end;
   a guidewire shaft having a proximal end and a distal end, the guidewire shaft defining a guidewire lumen, the guidewire shaft being coaxial with the catheter shaft, the guidewire shaft running longitudinally through the catheter shaft and extending distally beyond the distal end of the catheter shaft;
   an inflatable balloon having a proximal end and a distal end,
      a proximal balloon cone having a proximal end and a distal end,
      a distal balloon cone having a proximal end and a distal end,
      the proximal end of the balloon is attached to the distal end of the proximal balloon cone, the distal end of the balloon is attached to the proximal end of the distal balloon cone,
      a proximal tail having a proximal end, a distal end and an inner diameter, the proximal end of the proximal cone is affixed to the distal end of the proximal tail,
      a distal tail having a proximal end, a distal end and an inner diameter, the distal end of the distal cone is affixed to the proximal end of the distal tail,
      the proximal end of the proximal tail being mounted on to the distal end of the catheter shaft,
      the distal end of the proximal tail being affixed to the proximal end of the proximal balloon cone,
      the distal end of the distal tail being mounted on to the distal end of the guidewire shaft,
      the proximal end of the distal tail being affixed to the distal end of the distal balloon cone
      the balloon being in fluid communication with the inflation lumen; and
   a proximal stopper affixed to the outer diameter of the catheter shaft and forming an interference fit between the outer diameter of the catheter shaft and the inner diameter of the proximal tail, the proximal stopper being set back proximally of the proximal end of the proximal cone and distal to the proximal end of the proximal tail, the proximal stopper being annular in shape and being in length shorter than the proximal tail and the proximal stopper being of uniform circumferential thickness such that the inner diameter of the proximal tail is spaced a uniform distance from the outer diameter of the catheter shaft around the circumference of the catheter shaft so as to create a uniform proximal gap between the outer diameter of the catheter shaft and the inner diameter of the proximal tail, proximal to the proximal stopper, said proximal gap having adhesive therein to sealingly affix the proximal balloon tail to the catheter shaft.

2. The medical catheter of claim 1 wherein the proximal stopper is set back proximally of the proximal end of the proximal cone by at least approximately 0.25 mm.

3. The medical catheter of claim 1 wherein the proximal stopper is made from an adhesive material.

4. The medical catheter of claim 1 wherein the proximal stopper is made from a heat shrinkable material.

5. The medical catheter of claim 1 also comprises a proximal fillet made from an adhesive material placed at the proximal end of the proximal balloon tail, the proximal fillet tapering down from the proximal tail to the catheter shaft.

6. The medical catheter of claim 1 wherein the proximal stopper is not more than approximately 0.75 mm in length.

7. The medical catheter of claim 1 wherein the proximal stopper is made from a radiopaque material.

8. A medical catheter comprising:
   a catheter shaft defining an inflation lumen, the catheter shaft having an inner diameter, outer diameter, proximal end and distal end;
   a guidewire shaft defining a guidewire lumen, the guidewire shaft being coaxial with the catheter shaft, the guidewire shaft running longitudinally through the catheter shaft and extending distally beyond the distal end of the catheter shaft;

an inflatable balloon having a proximal tail having an inner diameter, a distal tail having an inner diameter, the proximal tail being mounted on to the distal end of the catheter shaft, the distal tail being mounted on to the guidewire shaft, the balloon being in fluid communication with the inflation lumen;

a stopper means sealingly affixed between the outer diameter of the catheter shaft and the inner diameter of the proximal tail, the stopper means being annular in shape and being in length shorter than the proximal tail and being of uniform circumferential thickness the stopper means is made from a radiopaque material; and an adhesive sealing a portion of the proximal tail, which is proximal to the stopper means, to the catheter shaft.

9. A medical catheter comprising:

a catheter shaft defining an inflation lumen, the catheter shaft having an inner diameter, outer diameter, proximal end and distal end;

a guidewire shaft having a proximal end and a distal end, the guidewire shaft defining a guidewire lumen, the guidewire shaft being coaxial with the catheter shaft, the guidewire shaft running longitudinally through the catheter shaft and extending distally beyond the distal end of the catheter shaft;

an inflatable balloon having a proximal end and a distal end,
   a proximal balloon cone having a proximal end and a distal end,
   distal balloon cone having a proximal end and a distal end,
   the proximal end of the balloon is attached to the distal end of the proximal balloon cone, the distal end of the balloon is attached to the proximal end of the distal balloon cone,
   a proximal tail having a proximal end, a distal end and an inner diameter, the proximal end of the proximal cone is affixed to the distal end of the proximal tail,
   a distal tail having a proximal end, a distal end and an inner diameter, the distal end of the distal cone is affixed to the proximal end of the distal tail,
   the proximal end of the proximal tail being mounted on to the distal end of the catheter shaft,
   the distal end of the proximal tail being affixed to the proximal end of the proximal balloon cone,
   the distal end of the distal tail being mounted on to the distal end of the guidewire shaft,
   the proximal end of the distal tail being affixed to the distal end of the distal balloon cone
   the balloon being in fluid communication with the inflation lumen;

a distal stopper affixed to the outer diameter of the guidewire shaft and forming an interference fit between the outer diameter of the guidewire shaft and the inner diameter of the distal tail, the distal stopper being proximal of the distal end of the distal tail and distal to the distal end of the distal balloon cone, the distal stopper being annular in shape and being in length shorter than the distal tail and the distal stopper being of uniform circumferential thickness such that the inner diameter of the distal tail is spaced a uniform distance from the outer diameter of the guidewire shaft around the circumference of the guidewire shaft, so as to create a uniform distal gap between the outer diameter of the guidewire shaft and the inner diameter of the distal tail, distal to the distal stopper, said distal gap having adhesive therein to sealingly affix the distal balloon tail to the guidewire shaft.

10. The medical catheter of claim 9 wherein a distal fillet of adhesive material is placed at the distal end of the distal balloon tail, the distal fillet tapering down from the distal tail to the guidewire shaft.

11. A medical catheter comprising:

a catheter shaft defining an inflation lumen, the catheter shaft having an inner diameter, outer diameter, proximal end and distal end;

a guidewire shaft having a proximal end and a distal end, the guidewire shaft defining a guidewire lumen, the guidewire shaft being coaxial with the catheter shaft, the guidewire shaft running longitudinally through the catheter shaft and extending distally beyond the distal end of the catheter shaft;

an inflatable balloon having a proximal end and a distal end,
   a proximal balloon cone having a proximal end and a distal end,
   a distal balloon cone having a proximal end and a distal end,
   the proximal end of the balloon is attached to the distal end of the proximal balloon cone, the distal end of the balloon is attached to the proximal end of the distal balloon cone,
   a proximal tail having a proximal end, a distal end and an inner diameter, the proximal end of the proximal cone is affixed to the distal end of the proximal tail,
   a distal tail having a proximal end, a distal end and an inner diameter, the distal end of the distal cone is affixed to the proximal end of the distal tail,
   the proximal end of the proximal tail being mounted on to the distal end of the catheter shaft,
   the distal end of the proximal tail being affixed to the proximal end of the proximal balloon cone,
   the distal end of the distal tail being mounted on to the distal end of the guidewire shaft,
   the proximal end of the distal tail being affixed to the distal end of the distal balloon cone
   the balloon being in fluid communication with the inflation lumen;

a proximal stopper affixed to the outer diameter of the catheter shaft and forming an interference fit between the outer diameter of the catheter shaft and the inner diameter of the proximal tail, the proximal stopper being set back proximally of the proximal end of the proximal cone and distal to the proximal end of the proximal tail, the proximal stopper being annular in shape and being in length shorter than the proximal tail and the proximal stopper being of uniform circumferential thickness, a portion of the proximal tail is located proximal to the stopper means such that the inner diameter of the proximal tail is spaced a uniform distance from the outer diameter of the catheter shaft around the circumference of the catheter shaft so as to create a uniform proximal gap between the outer diameter of the catheter shaft and the inner diameter of the proximal tail, proximal to the proximal stopper, said proximal gap having adhesive therein to sealingly affix the proximal balloon tail to the catheter shaft; and a distal stopper affixed to the outer diameter of the guidewire shaft and forming an interference fit between the outer diameter of the guidewire shaft and the inner diameter of the distal tail, the distal stopper being proximal of the distal end of the distal tail and distal to the distal end of the distal balloon cone, the distal stopper being annular in shape and being in length shorter than the distal tail and the distal stopper being of uniform circumferential thickness such that the inner diameter of the distal tail is spaced a uniform distance from the outer diameter of the guidewire shaft around the circumference of the guidewire shaft, so as to create a uniform distal gap between the outer diameter of the guidewire shaft and the inner diameter of the distal tail distal to the distal stopper, said distal gap having adhesive therein to sealingly affix the distal balloon tail to the guidewire shaft.

12. The medical catheter of claim 9 or 11 wherein the distal stopper is set back distally of the distal end of the distal cone by at least approximately 0.25 mm.

13. The medical catheter of claim 9 or 11 wherein the distal stopper is made from an adhesive material.

14. The medical catheter of claim 9 or 11 wherein the distal stopper is made from a heat shrinkable material.

15. The medical catheter of claim 9 or 11 wherein the distal stopper is not more than approximately 0.75 mm in length.

16. The medical catheter of claim 11 wherein the proximal stopper is set back proximally of the proximal end of the proximal cone by at least approximately 0.25 mm.

17. The medical catheter of claim 11 wherein the proximal stopper is made from an adhesive material.

18. The medical catheter of claim 11 wherein the proximal stopper is made from a heat shrinkable material.

19. The medical catheter of claim 18 wherein the distal stopper is made from a radiopaque material.

20. The medical catheter of claim 11 also comprises a proximal fillet made from an adhesive material placed at the proximal end of the proximal balloon tail, the proximal fillet tapering down from the proximal tail to the catheter shaft.

21. The medical catheter of claim 11 wherein the proximal stopper is not more than approximately 0.75 mm in length.

22. The medical catheter of claim 11 wherein the proximal stopper is made from a radiopaque material.

23. The medical catheter of claim 11 wherein the proximal stopper and the distal stopper are made from a radiopaque material.

24. A medical catheter comprising:

a catheter shaft defining an inflation lumen, the catheter shaft having an inner diameter, outer diameter, proximal end and distal end;

a guidewire shaft defining a guidewire lumen, the guidewire shaft being coaxial with the catheter shaft, the guidewire shaft running longitudinally through the catheter shaft and extending distally beyond the distal end of the catheter shaft;

an inflatable balloon having a proximal tail having an inner diameter, a distal tail having an inner diameter, the proximal tail being mounted at the distal end of the catheter shaft, the distal tail being mounted on the guidewire shaft, the balloon being in fluid communication with the inflation lumen;

a stopper means being sealingly affixed between the outer diameter of the guidewire shaft and the inner diameter of the distal tail, the stopper means being annular in shape and being in length shorter than the distal tail and being of uniform circumferential thickness the stopper means is made from a radiopaque material; and an adhesive sealing a portion of the distal tail, which is distal to the stopper means, to the guidewire shaft.

* * * * *